United States Patent [19]

MacMahon

[11] Patent Number: 5,241,578
[45] Date of Patent: Aug. 31, 1993

[54] OPTICAL GRID ALIGNMENT SYSTEM FOR PORTABLE RADIOGRAPHY AND PORTABLE RADIOGRAPHY APPARATUS INCORPORATING SAME

[75] Inventor: Heber MacMahon, Chicago, Ill.

[73] Assignee: ARCH Development Corporation, Chicago, Ill.

[21] Appl. No.: 801,189

[22] Filed: Dec. 2, 1991

[51] Int. Cl.$^5$ ............................................. G21K 1/00
[52] U.S. Cl. ..................................... 378/154; 378/206
[58] Field of Search ................. 378/205, 206, 154, 155

[56] References Cited

U.S. PATENT DOCUMENTS

| | | |
|---|---|---|
| 2,111,903 | 3/1938 | Rona . |
| 2,355,066 | 8/1944 | Goldfield et al. . |
| 3,304,427 | 2/1967 | Peyser ................................ 378/206 |
| 3,705,984 | 12/1972 | Westenberger . |
| 3,979,595 | 9/1976 | Merchant . |
| 4,092,544 | 5/1978 | Grim . |
| 4,246,486 | 1/1981 | Madsen . |
| 4,380,087 | 4/1983 | Tanaka . |
| 4,455,672 | 6/1984 | Hahn et al. . |
| 4,563,589 | 1/1986 | Jordan . |
| 4,752,948 | 6/1988 | MacMahon . |

OTHER PUBLICATIONS

Advertisement titled "Precision Plus," by Gammex Lasers (1989).
Heber MacMahon, "Friday Morning, Arie Crown Theatre," Scientific Sessions, pp. 249 and 360, Nov. 30, 1990.

*Primary Examiner*—Craig E. Church
*Attorney, Agent, or Firm*—Arnold, White & Durkee

[57] ABSTRACT

An optical alignment system for aligning a film cassette carrying grid cassette with an x-ray source of a portable x-ray apparatus. To facilitate accurate alignment of the central x-ray beam of the x-ray source of a portable x-ray apparatus with a focused grid in a clinical setting, the present invention uses a light projector and a reflector device. The light projector is substantially fixed relative to the x-ray source and projects a spot or line of light on the surface of the grid cassette. The reflector device, which can be temporarily or permanently fixed to the grid cassette, includes a reflector surface and an image surface. Images of the incident light spot or line and of the reflected light spot or line are formed on the image surface, and the distance between the images indicates the magnitude of angulation alignment error between the grid cassette and the x-ray source. When beam alignment is accurate, the incident light spot or line and reflected light spot or line will be substantially superimposed, producing a single image on the reflector element. In addition, an opaque line on the transparent front surface of the collimator housing of the x-ray apparatus appears as a dark shadow within the field projected by the collimation light. Coincidence between the incident light spot or line and the shadow produced by the opaque line on the collimator serves as a distance indicator facilitating the placement of the grid cassette at the proper focal distance from the x-ray source. Further aspects of the invention include radiopaque markers which are located on front and rear surfaces of the grid cassette, and which produce images on an x-ray film when exposed. The relative positions between the images of the markers on the exposed radiographs are indicative of the amount of angulation alignment error between the grid cassette and the x-ray source. Yet another aspect of the present invention is the capability of the grid cassette to accommodate a standard x-ray film cassette in either a horizontal or vertical orientation, without reorienting the grid cassette itself.

19 Claims, 8 Drawing Sheets

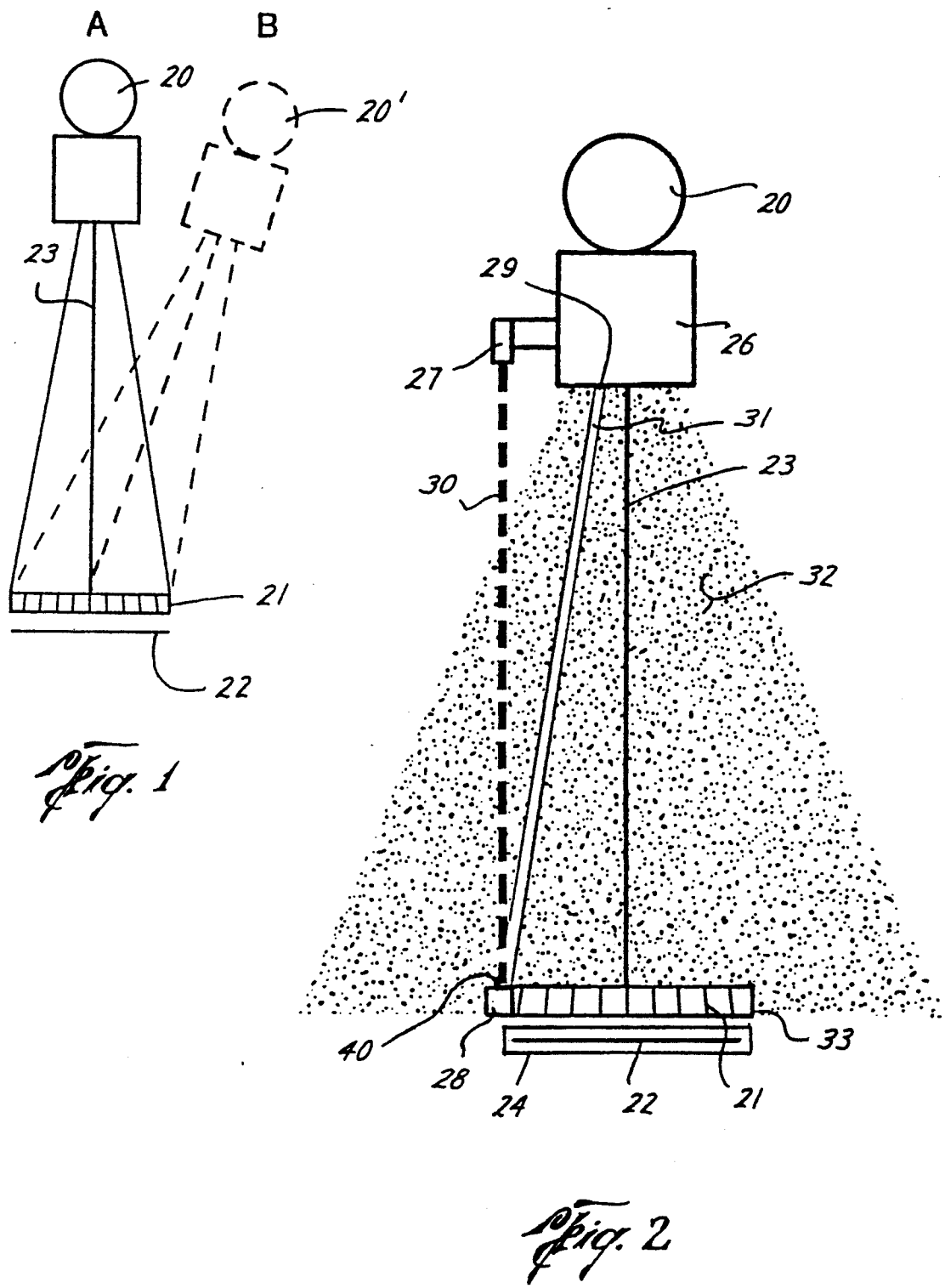

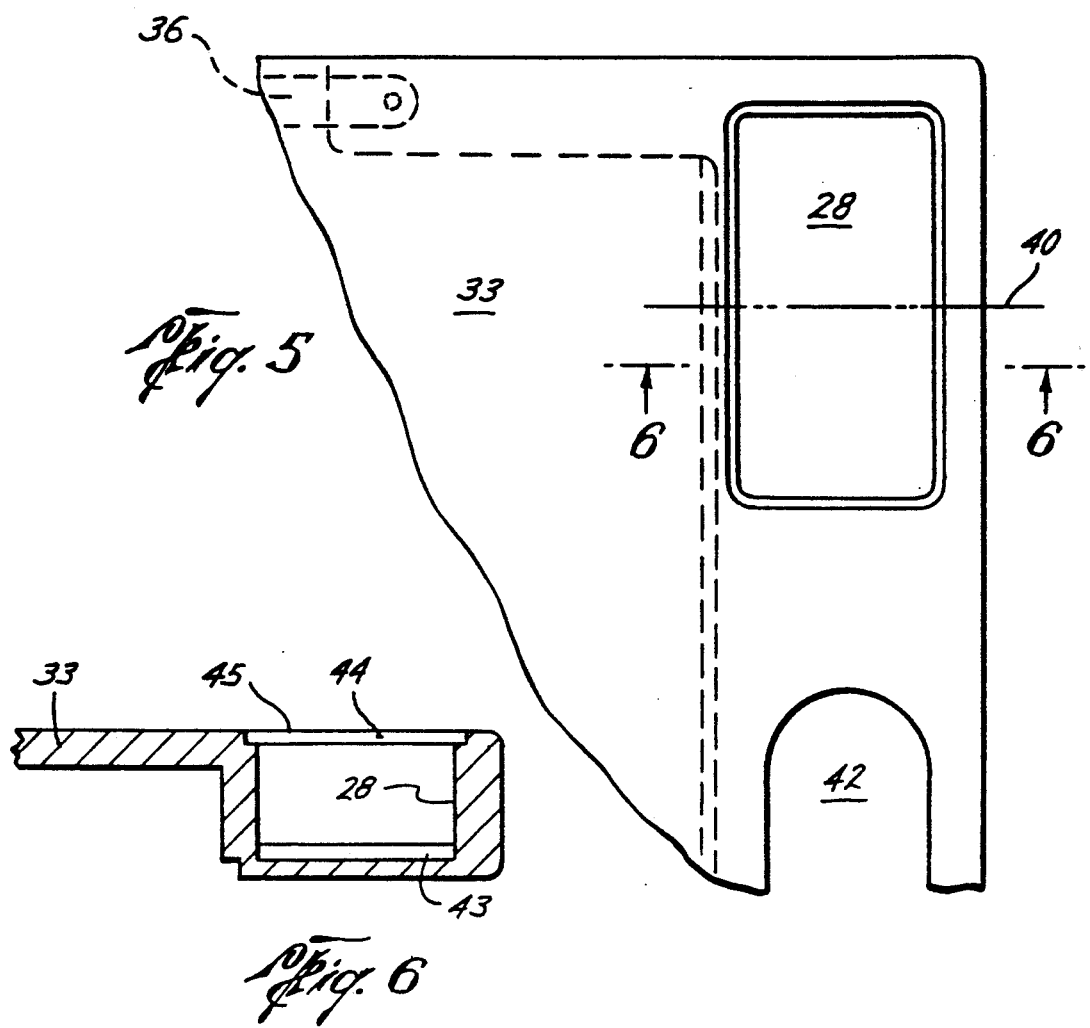
Fig. 5
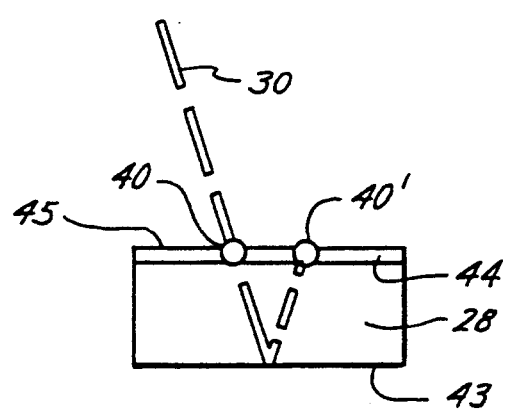
Fig. 6
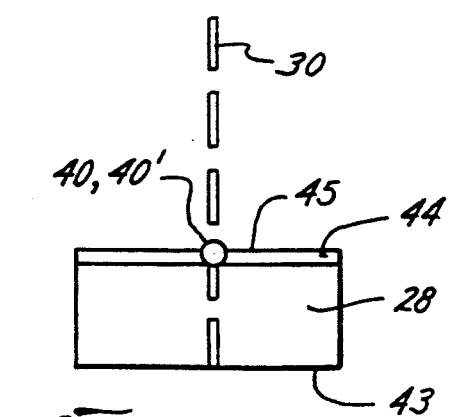
Fig. 7A
Fig. 7B

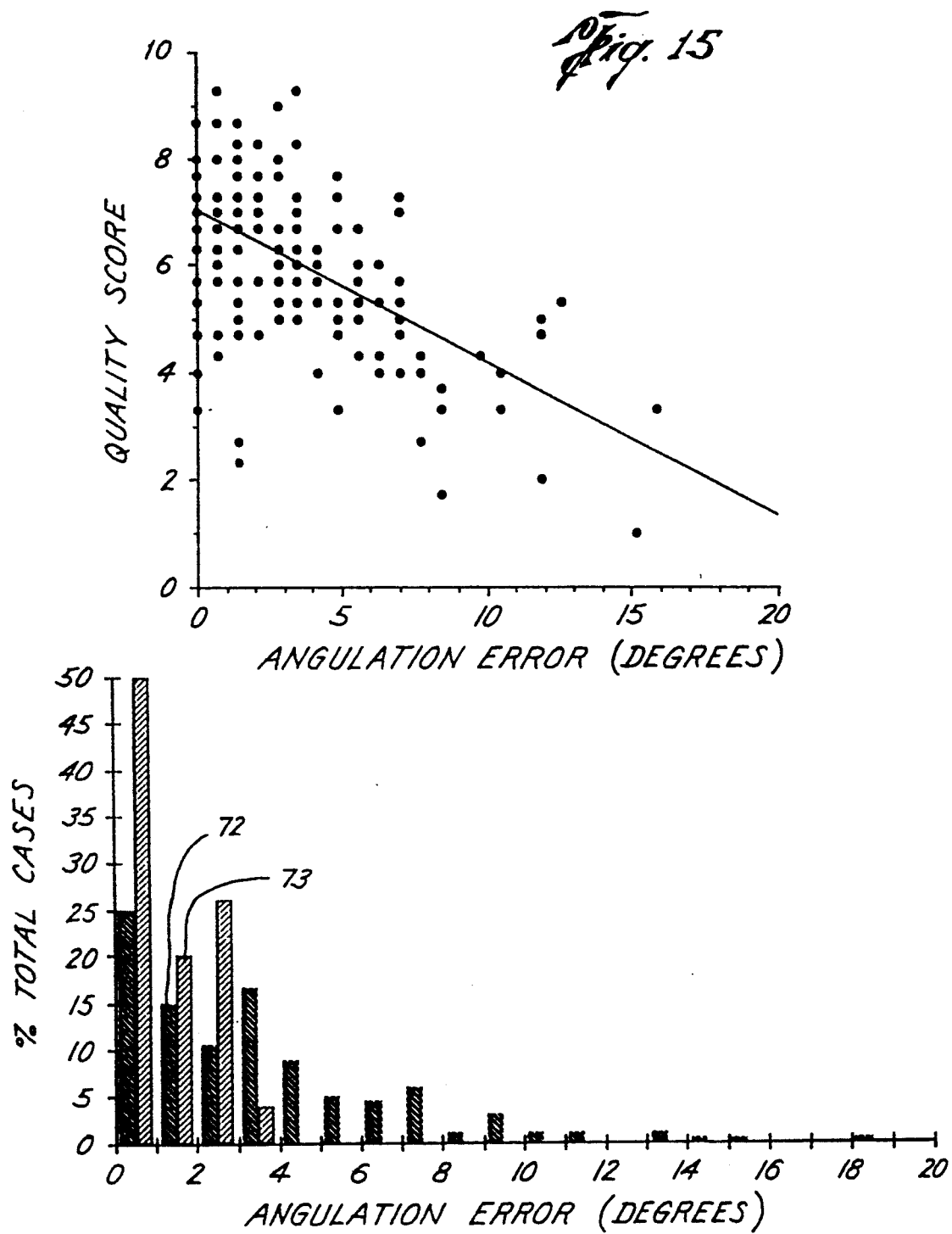

OPTICAL GRID ALIGNMENT SYSTEM FOR PORTABLE RADIOGRAPHY AND PORTABLE RADIOGRAPHY APPARATUS INCORPORATING SAME

BACKGROUND OF THE INVENTION

The present invention relates to a grid alignment system for portable radiography.

Portable radiography accounts for an increasing proportion of x-ray examinations performed in hospitals. In the University of Chicago hospitals, approximately 50% of all chest radiographs are obtained at the bedside with portable radiographic apparatus. Though the clinical importance of these examinations is beyond question, the image quality is generally inferior to that obtained with fixed radiographic apparatus in an x-ray department. The inferior image quality obtained using portable radiography apparatus is widely recognized, and is a source of concern to radiologists and clinicians. This poor image quality is commonly attributed to intrinsic limitations of portable radiography apparatus, however, it is in fact mainly due to uncontrolled scattered radiation, which fogs the radiograph, reducing contrast and obscuring diagnostic information.

Use of an accurately aligned anti-scatter grid can provide consistently high image quality, but precise alignment of the grid relative to the x-ray source is essential for good results. Such precise alignment is difficult to achieve with conventional manual or "eyeball" techniques.

For portable radiography, excellent results can be achieved with a 6:1 or 8:1 anti-scatter grid, provided that the x-ray beam energy is no greater than 90 KV, and provided that the anti-scatter grid is accurately aligned with respect to the x-ray source. Referring to FIG. 1, accurate alignment of portable radiographic machine 20 relative to anti-scatter grid 21 and x-ray film 22 is illustrated in position A, while inaccurate alignment is illustrated in position B.

In the case of a conventional lead strip linear anti-scatter grid, alignment is critical only in one dimension, that is, across the grid lines. Moderate angulation error along the direction of the grid lines does not significantly impair image quality. In other words, referring again to FIG. 1, moderate misalignment about a horizontal axis lying within the plane of the page is not so critical, whereas alignment about an axis perpendicular to the plane of the page is critical. Further, with a focused grid, it is also necessary for central x-ray beam 23 of portable x-ray machine 20 to be centered accurately with respect to anti-scatter grid 21. Further, variations in focus distance are important, but mainly affect film density, provided that the portable x-ray machine 20 is properly centered and aligned relative to anti-scatter grid 21. In the case of a two dimensional grid, for example a cross-hatch grid or pinhole grid, alignment is critical in two dimensions.

A system that addresses this alignment problem is presented in U.S. Pat. No. 4,752,948, issued Jun. 21, 1988, and assigned to the same assignee as the present application. The disclosure of U.S Pat. No. 4,752,948 is expressly incorporated herein by reference. While adequately addressing the problem of alignment between x-ray beam and anti-scatter grid in a portable x-ray apparatus, this patented device presents a mechanical system which has proven somewhat difficult to retrofit to existing portable x-ray apparatus, or to use with very ill patients who are unable to cooperate.

Therefore, a need exists for a simple alignment system which can be easily retrofitted to existing portable x-ray apparatus, and which can be used in the most difficult clinical situations.

Commercially available grid cassettes (x-ray film holders incorporating anti-scatter grids) include a 14×17 inch (35.6×43.2 cm) lead strip grid encased in nylon/plastic material. These grid cassettes are relatively crudely manufactured and are heavy and cumbersome to handle. When the grid lines are oriented vertically, the total transverse dimension of the grid is 14 inches (35.6 cm). Therefore, in heavy-set broad patients, it is necessary to rotate the grid cassette 90° so that the grid lines run transversely, orienting the longer dimension of the grid horizontally. This maneuver, which has been found to be necessary in between 25% and 50% of portable chest radiographs, frequently results in severe misalignment. This is so because the necessary vertical adjustments which must be performed accurately to align the x-ray beam with the grid are more difficult to judge accurately when the grid is transversely oriented. In addition, transversely orienting the grid requires the x-ray source and collimator to be rotated, an additional adjustment step.

Therefore, it would also be desirable to maintain the anti-scatter grid orientation in a vertical direction for all patients, while permitting the x-ray film to be oriented either vertically or horizontally facilitating the accommodation of heavy-set broad patients.

SUMMARY OF THE INVENTION

The present invention in large part avoids the above-noted problems of the prior approaches to alignment between a portable x-ray apparatus and an anti-scatter grid by providing a simple grid alignment system, which can be retrofitted to existing equipment. In addition, the invention provides a new grid cassette which facilitates the horizontal or vertical orientation of x-ray film in portable radiography, while permitting the anti-scatter grid to maintain a single orientation.

To facilitate accurate alignment and centering of the central x-ray beam with a focused grid in a clinical setting, the present invention employs a light projector, specifically, a laser light projector, and a unique compact reflector element. The projector is mounted in or on the collimator housing of a portable x-ray machine, and can be powered from the collimation light circuit or from a separate battery. The light projector is positioned so that a light line or spot is projected parallel to the central x-ray beam of the x-ray source. An opaque line on the transparent front surface of the collimator housing appears as a dark shadow within the field projected by the collimation light. The coincidence of this dark shadow with the laser light is indicative of placement of the grid cassette at the proper focal distance from the x-ray source. Angulation errors between the x-ray source and grid cassette are indicated by a compact reflector element which either temporarily attaches to or is formed integrally with the grid cassette. The front of the reflector element is covered by an imaging surface, and a reflecting surface is located behind the imaging surface. The incident light line or spot creates an image on the imaging surface, and the light line or spot reflected from the reflecting surface also forms an image on the imaging surface. The amount of separation between the two images on the imaging surface is indicative of the magnitude of angulation alignment error between the grid cassette and the x-ray source. When alignment is accurate, the incident light line or spot and reflected light line or spot are superimposed on the imaging surface.

To confirm the accuracy of beam alignment, the present invention contemplates at least one pair of small radiopaque markers which are inserted into the front and rear surfaces of the grid cassette. Each pair of markers is positioned so that when the x-ray beam is perfectly aligned and centered, the images produced by the markers on the x-ray film are substantially superimposed. Misalignment or decentering of the x-ray beam results in misregistration of the markers, and the amount of misalignment can be quantified by assessing the amount of misregistration.

The present invention also contemplates a grid cassette which is capable of accommodating either vertically or horizontally oriented film cassettes without requiring reorientation of the grid cassette. This allows accommodation of broad, heavyset patients without the misalignment errors that typically occur when the grid cassette is reoriented. The grid cassette also includes an integrally formed hand hold for easy portability and to facilitate placing the grid cassette behind a patient.

These and other features and advantages of the present invention will become apparent to one of skill in this art with reference to the drawings and following detailed description of the preferred embodiments.

BRIEF DESCRIPTION OF THE DRAWINGS

FIG. 1 is a schematic representation of misalignment between a portable radiography machine and a grid cassette.

FIG. 2 is a schematic representation of a portable x-ray apparatus incorporating the optical alignment system of the present invention.

FIGS. 5 and 6 are the reflector element incorporated in the grid cassette of FIG. 3 in accordance with the present invention.

FIGS. 7A and 7B illustrate incorrect and correct alignment indications produced by the reflector element incorporated in the grid cassette of FIG. 3.

FIG. 15 is a graph of subjective x-ray image quality plotted against grid angulation alignment error.

FIG. 16 is a graph comparing a conventional portable x-ray alignment technique with that of the present invention.

DETAILED DESCRIPTION OF THE PREFERRED EMBODIMENTS

Figure 3:
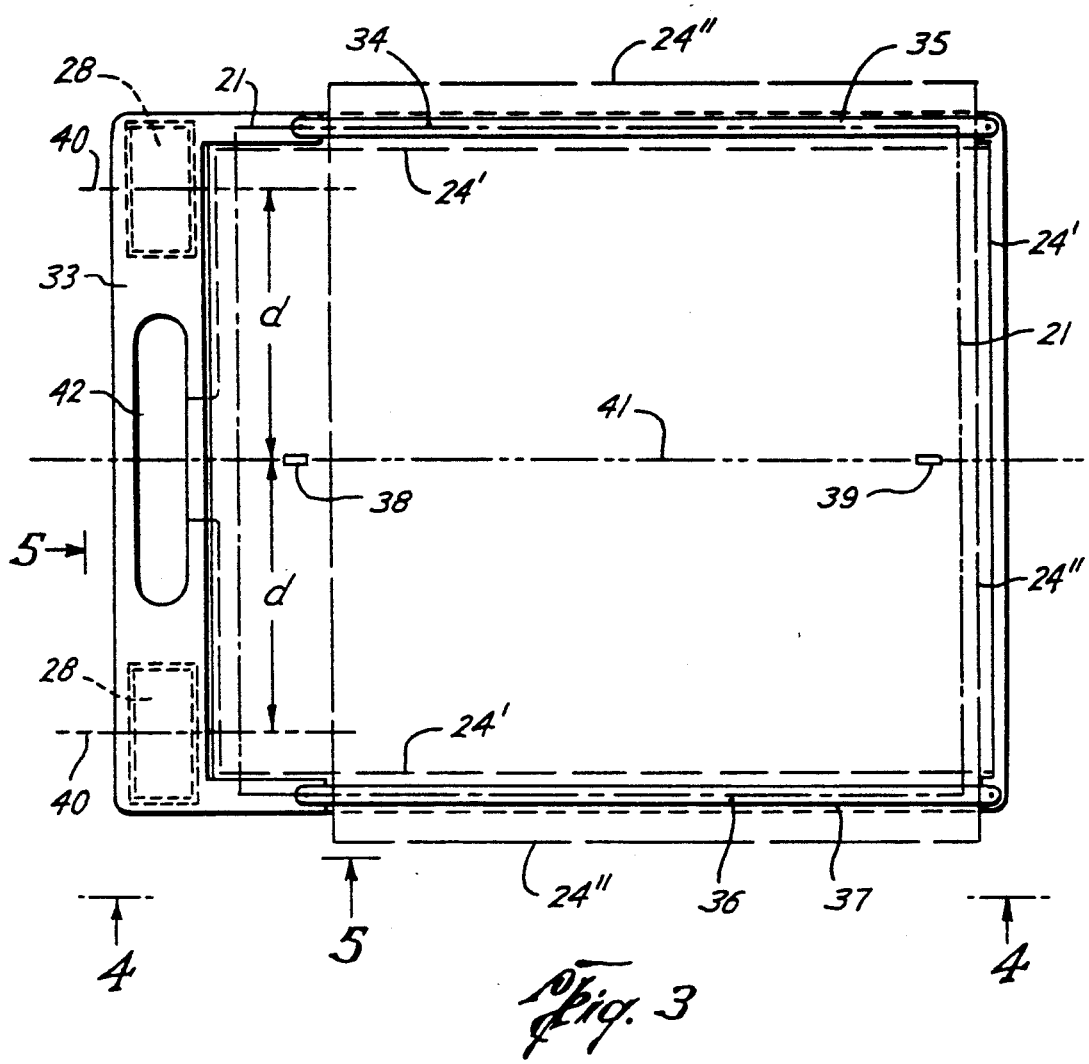
FIG. 3 is an embodiment of a grid cassette in accordance with the present invention.

Referring to FIG. 2, presented is a block diagram of a portable x-ray apparatus incorporating the optical alignment system of the present invention. The system includes x-ray machine 20 and grid cassette 33, including anti-scatter grid 21, which is located between x-ray machine 20 and x-ray film cassette 24 which holds x-ray film 22. Attached to collimator housing 26 of x-ray machine 20 is light projector 27 which projects light beam 30 which forms a line or spot of light on the surface of grid cassette 33. Included in or attached to grid cassette 33 is reflector element 28. Reflector element 28 and light projector 27 are located substantially equidistant from central x-ray beam 23. Further, opaque line 29 (shown in more detail with reference to FIG. 12) is applied to the transparent front surface of collimator housing 26, and casts a shadow 31 on the surface of grid cassette 33 within the collimation field projected by the collimation light within collimation housing 26.

As explained below in more detail, light projector 27, in combination with reflector element 28, ensures proper angulation alignment of grid cassette 33 relative to the x-ray source within portable x-ray machine 20. Further, when shadow 31 is coincident with light line or spot 40 projected from light projector 27 upon the surface of grid cassette 33, grid cassette 33 is located at the proper focal distance from the x-ray source within portable x-ray machine 20. Further, adjustment of grid cassette 33 so that light beam 30 impinges on grid cassette 33 at a predetermined location (for example, the middle of reflector element 28), ensures centering of x-ray machine 20 with respect to grid cassette 33. In addition, and explained in more detail below, grid cassette 33 is configured to hold film cassette 24 in either a vertical or horizontal position, without changing the orientation of grid cassette 33 relative to light projector 27 and portable x-ray machine 20.

Figure 4:
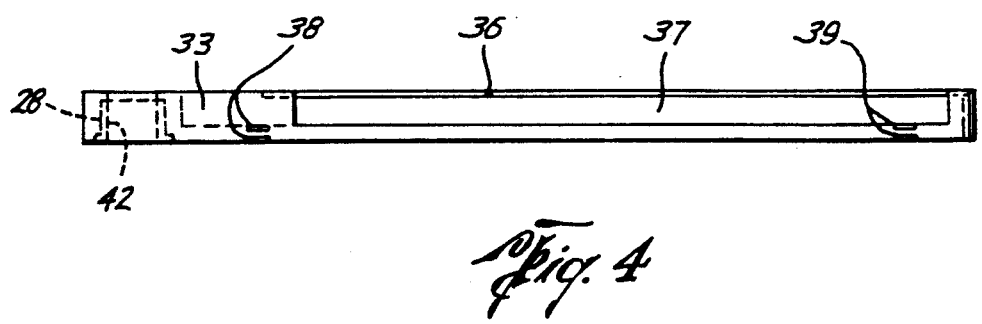
FIG. 4 is a view of the grid cassette of FIG. 3 from perspective 4—4.

Referring now to FIGS. 3 and 4, disclosed is an embodiment of grid cassette 33 in accordance with the present invention. In operation, x-rays from portable x-ray machine 20 impinge upon grid cassette 33 from the backside in FIG. 3, and from the bottom side in FIG. 4. Within grid cassette 33 is included anti-scatter grid 21 which, in this embodiment, is a 6:1 focused linear grid. Grid cassette 33 is configured with bars 34 and 36, which define substantially rectangular apertures 35 and 37 sized to fit the short dimension (14 inch (35.6 cm)) of film cassette 24. This permits grid cassette 33 to accommodate film cassette 24 in either a vertical position (24') or in a horizontal position (24"). This allows grid cassette 33 to maintain a constant position relative to portable x-ray machine 20 (see also FIG. 1), while permitting film cassette 24 to be configured in either a normal horizontal position, or in a vertical position to accommodate broad heavyset patients.

As mentioned above, when using a linear grid, alignment is critical across the grid lines, and is less critical along the direction of the grid lines. The grid lines of grid 21 within grid cassette 33 runs substantially parallel to center line 41 which, in turn, is substantially parallel to the longitudinal direction of the lead slats in anti-scatter grid 21 contained within grid cassette 33.

Grid cassette 33 also includes two pairs 38, 39 of radiopaque markers which permit an assessment of the accuracy of x-ray beam alignment. Pairs 38 and 39 of radiopaque markers are preferably made of tantalum, but can be of any radiopaque material. The preferred dimensions for each marker of pairs 38 and 39 are 1×3×0.7 mm, but the markers can be of any dimension or shape. Pairs 38 and 39 of radiopaque markers are discussed below in more detail with respect to FIGS. 8A and 8B and 9A and 9B.

Also included in grid cassette 33 are reflector elements 28, shown in more detail in FIGS. 5 and 6. Reflector elements 28 are located a distance d from center line 41 of grid cassette 33. In accordance with the present invention, distance d is substantially equal to the distance between the line or spot generated by light projector 27 and central x-ray beam 23 (see FIG. 2) and in the embodiment shown in FIG. 3, d, is preferably 6.5 inches (16.5 cm). The construction of reflector elements 28 is presented below in more detail with reference to FIGS. 5 and 6. Finally, grid cassette 33 includes hand hold 42 to facilitate the handling of grid cassette 33, and the positioning of grid cassette 33 behind a patient. Although two reflector elements 28 are included in grid cassette 33 of FIG. 3, only one is used at any one time for alignment purposes, and the other is included to accommodate other orientations between grid cassette 33 and x-ray machine 20.

Referring now to FIGS. 5 and 6, the details of reflector elements 28 are presented. The view of FIG. 5 is from the backside of grid cassette 33 shown in FIG. 3 (i.e., from the same side as portable x-ray machine 20 (see FIG. 2)), and FIG. 6 is taken through section 6—6 of FIG. 5.

Reflector element 28 is substantially rectangular in shape, and in the preferred embodiment is 1.5 wide×3 long×1 inch deep (3.8×7.6×2.5 cm). Located in the bottom of reflector element 28 is a reflecting surface, such as mirror 43, and covering a top of reflector element 28 is cover 44 which is preferably substantially transparent, and which is preferably made from Lexan brand plastic material. Cover 44 supports imaging surface 45 which is preferably a porous layer which allows light to pass therethrough while allowing a light image to form thereon. An exemplary material is a thin elastic vinyl material, such as rear projection screen material available from the Edmond Scientific Company. Alternatively, cover 44 and imaging surface 45 can be combined into a single unit. For example, the surface of cover 44 could be frosted, or cover 44 could be translucent. As mentioned above, light projector 27 projects light line or spot 40 onto the surface of grid cassette 33 where reflector elements 28 are located. The projection of light line or spot 40 onto reflector elements 28 facilitates alignment of grid cassette 33 relative to portable x-ray machine 20, as presented more clearly with reference to FIGS. 7A and 7B.

In FIG. 7A, light beam 30 projected from light projector 27 forms incident light line or spot 40 on imaging surface 45 of reflector element 28. Light beam 30 continues through cover 44 and is reflected by mirror 43 and back through cover 44 to produce reflected light line or spot 40' on imaging surface 45. The existence of two light images 40, 40' on imaging surface 45 of reflector element 28 is indicative of misalignment between grid cassette 33 and portable x-ray machine 20. The magnitude of misalignment is indicated by the amount of separation of images 40, 40' appearing on imaging surface 45 of reflector element 28.

When grid cassette 33 and portable x-ray machine 20 are correctly aligned, as illustrated by the representation of FIG. 7B, light beam 30 is reflected back upon itself when it strikes mirror 43 thus rendering images 40 and 40' substantially collinear. Use of a light line for alignment is more clearly illustrated below with reference to FIGS. 13A and 13B, and use of a light spot for alignment is more clearly illustrated below with reference to FIGS. 14A, B and C.

Figure 8A:
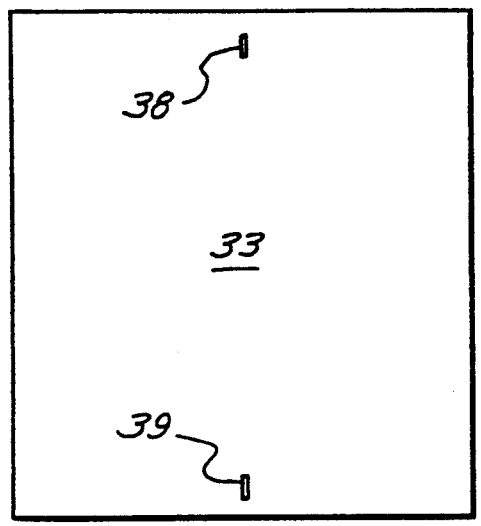
FIGS. 8A and 8B more clearly illustrate the placement of the alignment markers incorporating a grid cassette, in accordance with the present invention.
Figure 8B:
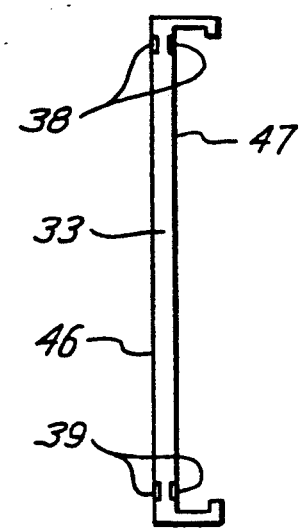
Figure 9A:
FIGS. 9A and 9B illustrate alignment and misalignment indications produced on a radiograph by the alignment markers, in accordance with the present invention.
Figure 9B:

Referring now to FIGS. 8A and 8B, the positioning of radiopaque marker pairs 38 and 39 is presented in more detail. Radiopaque marker pairs 38 and 39 are positioned within front surface 46 and rear surface 47 of grid cassette 33 so that shadows of the individual markers of radiopaque marker pairs 38 and 39 will appear on a developed x-ray film that was exposed while being held in grid cassette 33. The individual radiopaque markers of each pair of markers 38 and 39 are positioned in front surface 46 and in rear surface 47 of grid cassette 33 so that when the x-ray beam is properly aligned and centered, the resultant shadows on the radiograph will be substantially superimposed as illustrated in FIG. 9A. Misalignment or decentering of the x-ray beam relative to grid cassette 33 will result in misregistration of the images of marker pairs 38 and 39, as illustrated in FIG. 9B. Such misalignment can be quantified with a calibrated magnifying loupe, and alignment errors can be determined in both vertical and horizontal dimensions within 1°. The horizontal axes of the graphs of FIGS. 15 and 16, described in more detail below, were determined in this manner.

Although two pairs 38, 39 of radiopaque markers are preferred, it will be understood that only one pair is necessary to accomplish the purposes of the present invention. Use of two pairs of markers increases the chances that at least one of the pairs will appear on a radiograph. In addition, if both pairs are visible, the distance between the pairs on the radiograph relative to the distance between the pairs on the grid is indicative of the focal distance at which the radiograph was exposed.

Figure 10:
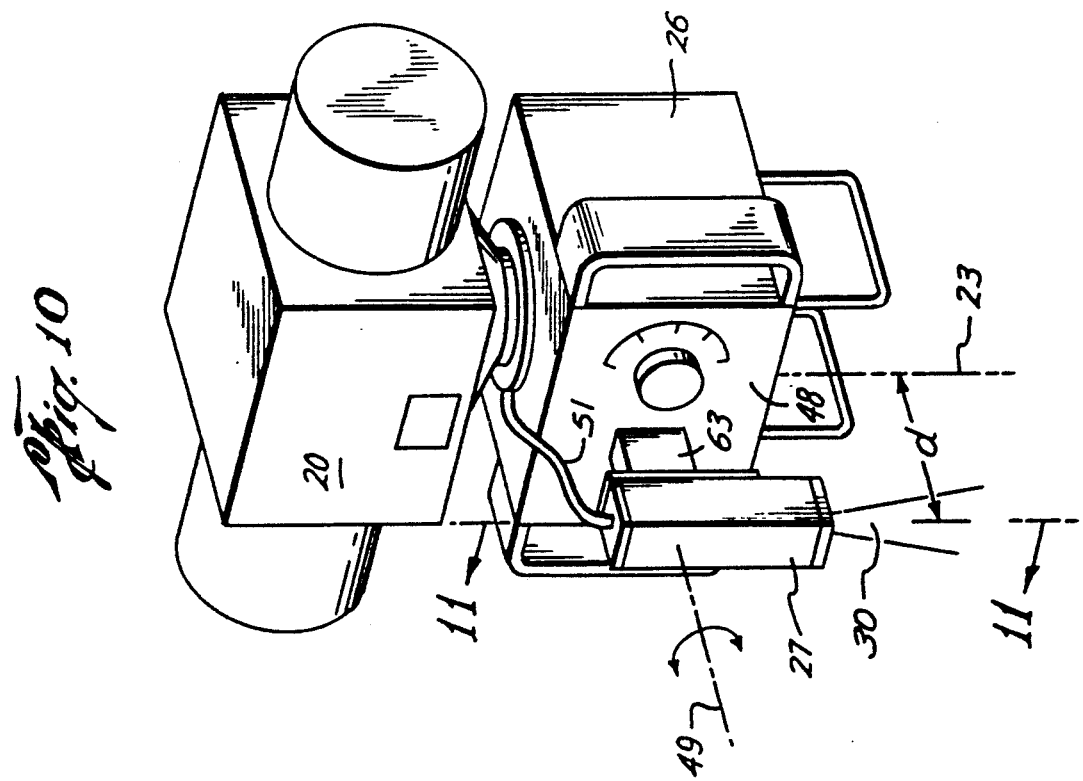
FIG. 10 is the light projector of the present invention mounted on a portable x-ray machine collimator.

Referring now to FIG. 10, presented in more detail is the configuration of portable x-ray machine 20, collimator housing 26 and light projector 27 in accordance with the present invention. In FIG. 10, light projector 27 is shown mounted to face plate 48 of collimator housing 26 of a conventional portable x-ray machine, for example, a type AMX 4, portable x-ray machine available from the General Electric Company. The present invention, of course, could be used with other types of portable x-ray machines, and light projector 27 could be integrated within collimator housing 26, rather than mounted to face plate 48. As described above with reference to FIG. 2, light projector 27 projects light beam 30. Light beam 30 is fan-shaped when projecting a line, and is substantially circular or elliptical in cross-section when projecting a spot, and is projected in a plane which is substantially parallel to face plate 48 and central x-ray beam 23. Light projector 27 is positioned relative to central x-ray beam 23 so that light beam 30 is projected at a distance, d, from central x-ray beam 23. This distance, d, is the same as distance, d, shown in FIG. 3 between center line 41 of grid cassette 33 and light line or spot 40 projected on the surface of grid cassette 33.

Light projector 27 is rotatable slightly about axis 49 in order to project light beam 30 to one edge, or the other, of grid cassette 33. In operation, a technician will rotate light projector 27 about axis 49, until light beam 30 strikes the surface of grid cassette 33 to form light line or spot 40 upon reflector element 28, as shown in FIG. 3. Light projector 27 is powered through power cable 51 from the collimation light circuit within collimator housing 26 and is activated whenever the collimation light within collimator housing 26 is activated. Alternatively, light projector 27 could be powered from a battery pack to simplify retrofitting existing x-ray machines.

Figure 11:
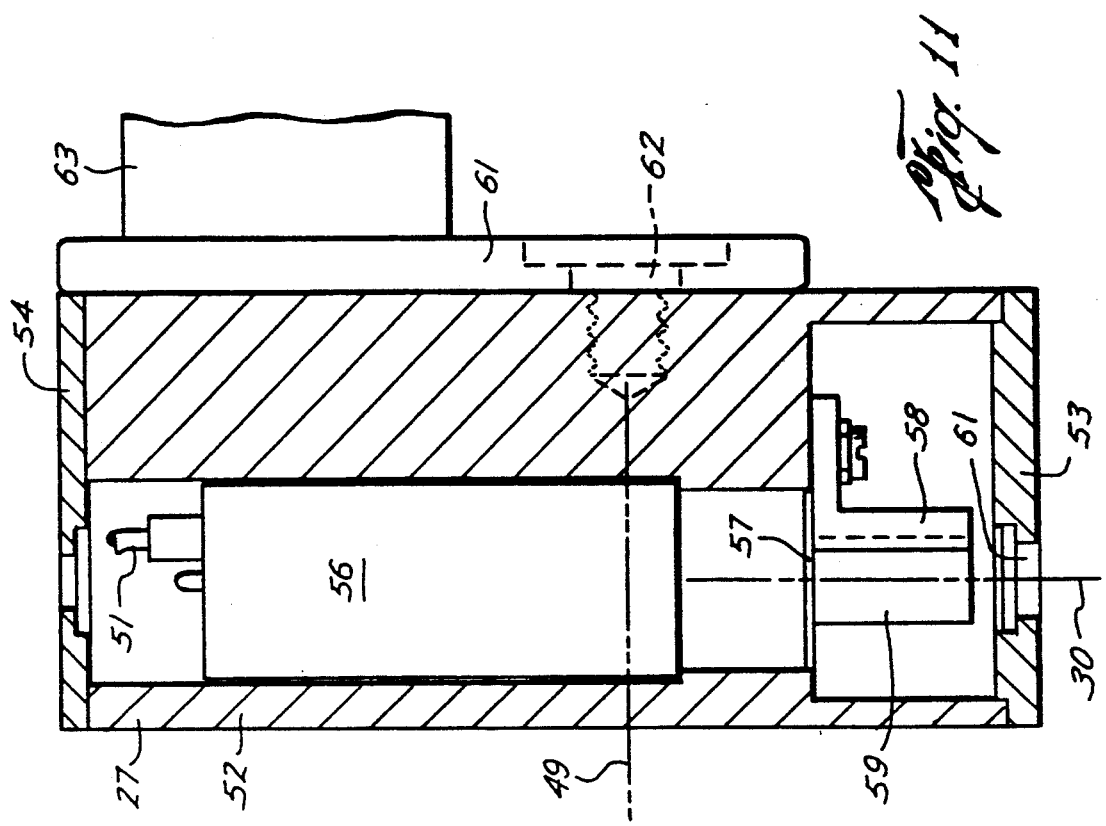
FIG. 11 is an embodiment of the light projector of the present invention, illustrated in more detail.

FIG. 11 presents a view through section 11—11 of light projector 27 in FIG. 10. Light projector 27 includes housing 52 with front cover plate 53 and rear cover plate 54. Housing 52 and plates 53 and 54 can be machined, cast or molded from aluminum, or plastic, or other suitable material. Within housing 52 is mounted solid state laser 56 which is powered, as described above, through power cable 51. Solid state laser 56 is preferably a LAS-200-670-5 type laser available from the Laser Max Company of Rochester, N.Y., which emits laser light beam 57 at 670 nanometers, with a power of 4.75 milliwatts. Laser light beam 57 is substantially elliptical in cross-section, with dimensions of approximately 0.8×3.3 millimeters.

Behind front cover plate 53 is mounted lens mount 58 upon which is mounted cylinder lens 59. Cylinder lens 59 converts laser light beam 57 into fan-shaped light beam 30 which is projected from light projector 27 through optical window 61 mounted in front cover plate 53. Fan-shaped light beam 30 lies in a plane which is substantially perpendicular to the plane of the page of FIG. 11. Alternatively, when projecting a spot, lens mount 58 and cylinder lens 59 can be eliminated, allowing light beam 57 to pass directly through optical window 61.

Although in the preferred embodiment, a solid state laser light source is used, it will be understood by those of skill in this art that other types of light sources, including non-laser light sources, could be used, without departing from the spirit and scope of the invention, as long as light projector 27 projects a line or spot of light onto reflector elements 28 mounted in or on grid cassette 33 (see also FIG. 2).

Light projector 27 is pivotally mounted to pivot plate 61 by pivot pin 62 to allow rotation of light projector 27 about axis 49 (also see FIG. 10). Pivot plate 61 is connected to a first end of spacer 63, the second end of which (not shown) is mounted to face plate 48 of collimator 26 (see FIG. 10).

Figure 12:
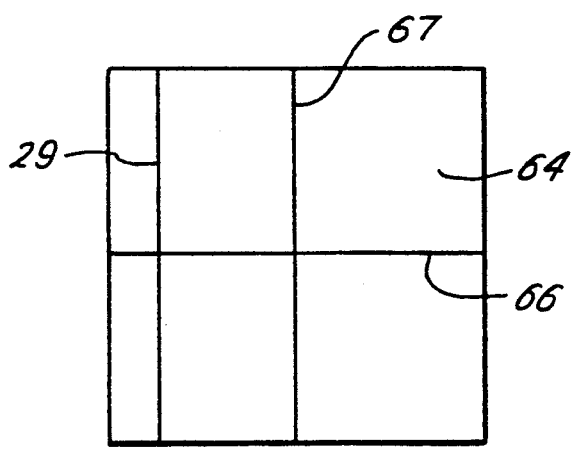
FIG. 12 is the transparent collimator front surface of a portable radiographic apparatus, in accordance with the present invention.

Referring now to FIG. 12, disclosed is the transparent cover plate 64 of collimator housing 26, in accordance with the present invention. Cover plate 64 includes standard cross-hairs 66, 67, the shadows of which are projected on a patient during the alignment of portable x-ray machine 20 (see also FIG. 2). The intersection of cross-hairs 67 and 68 is substantially coincident with central x-ray beam 23.

In accordance with the present invention, added to transparent cover plate 64 is opaque focus line 29 which, as described above, with reference to FIG. 2, casts a shadow onto the surface of grid cassette 33 holding anti-scatter grid 21. During alignment of portable x-ray machine 20 in accordance with the present invention, a technician will position portable x-ray machine 20 a distance from grid cassette 33 until the shadow 31 of opaque line 29 appearing on the surface of grid 33 coincides with light line or spot 40 produced by light beam 30. The focal distance depends upon the focus distance of the grid being used, and in the preferred embodiment the focal distance is 48 inches (122 cm). In addition, to ensure proper centering of grid cassette 33 and central x-ray beam 23, grid cassette 33 is moved until light line or spot 40 strikes a predetermined portion of grid cassette 33, for example, the center of reflector element 28.

Figure 13A:
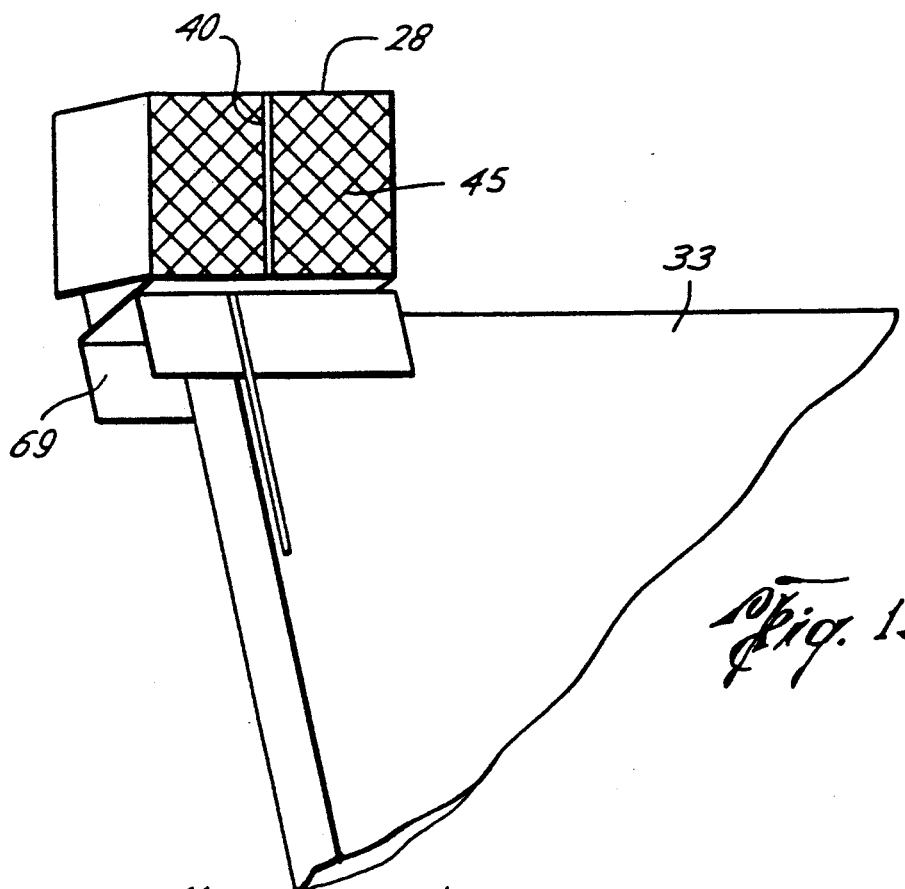
FIGS. 13A and 13B are an alternate embodiment of the reflector element of the present invention.
Figure 13B:
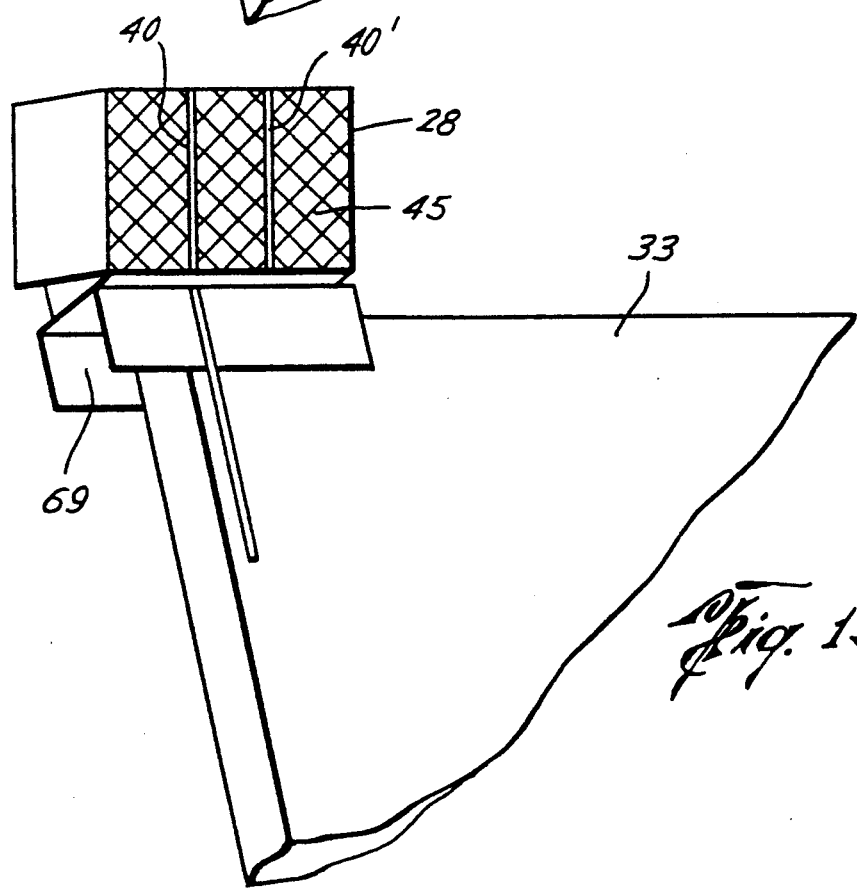

Referring now to FIGS. 13A and 13B, presented is an alternative embodiment of reflector element 28, in accordance with the present invention. In FIGS. 13A and 13B, rather than being integrally formed with grid cassette 33 as shown in FIG. 3, reflector element 28 is mounted temporarily to grid cassette 33 by use of bracket 69 and magnets (not shown). In the embodiment shown in FIGS. 13A and 13B, reflector element 28 is temporarily mounted to a corner of grid cassette 33, and during the alignment procedure, light line 40 is projected onto reflector element 28. Reflector element 28 shown in FIGS. 13A and 13B is a substantially rectangular-shaped box with a light reflecting surface (not shown) located in a bottom thereof. Imaging surface 45, supported by a transparent plastic plate, facilitates the viewing of light line 40. In FIG. 13A, the single light line 40 indicates accurate alignment between grid cassette 33 and portable x-ray machine 20, whereas the existence of two light lines 40 and 40' shown in FIG. 13B is indicative of misalignment between grid cassette 33 and portable x-ray machine 20 (see also FIG. 2).

The embodiments described that use light line 40 are for the purpose of aligning a linear grid which requires alignment in only one dimension (i.e., across the grid lines). Two dimensional grids, for example crosshatched grids or pinhole grids, require alignment in two dimensions. In other words, referring again to FIG. 2, when using a two-dimensional grid, central x-ray beam 23 should be substantially perpendicular to the plane of grid cassette 33.

Figure 14A:
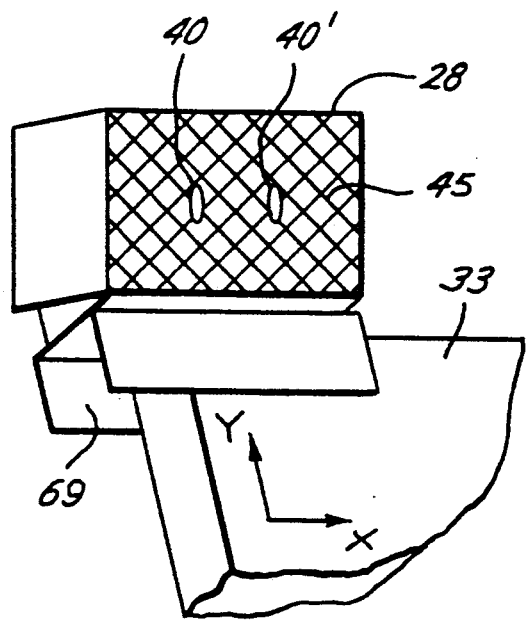
FIGS. 14A, 14B, and 14C present yet another alternative embodiment of the present invention.

In accordance with the present invention, to align central x-ray beam 23 and grid cassette 33 in two dimensions, a spot of light is projected by light projector 27. Alignment of grid cassette 33 using a light spot is illustrated in FIGS. 14A, B and C. In FIGS. 14A, B and C, reflector element 28 is the same as that used for linear grid alignment described earlier, and includes a light reflecting surface (not shown in FIGS. 14A, B and C) and an imaging surface 45. Reflector element 28 in FIGS. 14A, B and C is shown temporarily attached to grid cassette 33 with bracket 69. However, reflector element 28 may be integrally formed with grid cassette 33 as shown, for example, in FIGS. 3, 4, 5 and 6.

Figure 14B:
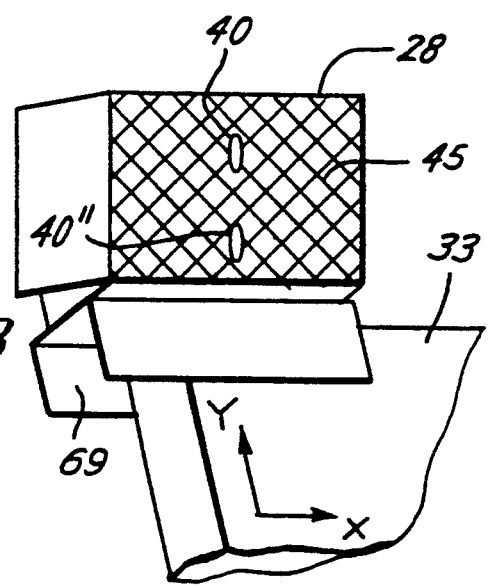
Figure 14C:
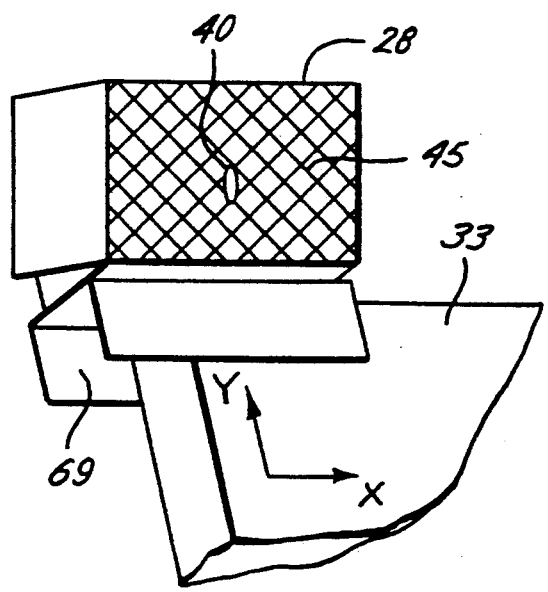

In FIG. 14A, separation between incident light spot 40 and reflected light spot 40' indicates misalignment about the y-axis (drawn on grid cassette 33) between grid cassette 33 and central x-ray beam 23 (see also FIG. 2). In FIG. 14B, separation between incident light spot 40 and reflected light spot 40'' indicates misalignment about the x-axis. The single light spot 40 shown in FIG. 14C indicates accurate alignment about both x- and y-axes. In other words, in FIG. 14C, central x-ray beam 23 is substantially perpendicular to the surface of grid cassette 33. Although light spots 40, 40', 40'' are elliptical as shown in FIGS. 14A, B and C, it will be understood that light spots of any shape could be used without departing from the scope of the invention.

To demonstrate the advantages of the alignment system of the present invention, 400 consecutive conventional portable chest x-ray examinations were identified and reviewed. Of these, 161 had been performed with images of tantalum markers (for example, like those shown in FIGS. 9A and 9B). With the images of the alignment markers obscured, three experienced chest radiologists reviewed the radiographs, and scored each case for overall subjective image quality, using a ten point scale where ten indicated the highest subjective quality, and one the lowest. The results are shown in the graph of FIG. 15. The angulation error plotted as the horizontal axis in FIG. 15 was calculated for each radiograph from the relative positions of the images of the radiopaque markers. As can be seen with reference to FIG. 15, all cases with the highest quality ratings also had accurate grid alignment. Several cases which were accurately aligned received a low quality rating, which was believed to be due to overexposure. However, no case with a large grid angulation error achieved a high quality rating, regardless of exposure.

In a separate experiment, grid alignment was determined retrospectively by use of the radiopaque markers for a random series of 200 portable chest radiographs obtained with conventional manual alignment techniques. The percentage of the total cases plotted versus angulation error in heavy cross-hatched bars 72 of the bar chart of FIG. 16. In several cases, excellent manual alignment was obtained, which was believed to be due to intensive technologist training, augmented by feedback provided by the radiopaque alignment markers. Also in FIG. 16 is the range of angulation alignment error for 50 consecutive portable chest radiographs obtained using the optical alignment system of the present invention, plotted with bars 73 having light cross-hatching. As can be seen with reference to FIG. 16, the range of angulation alignment error using the optical grid alignment system of the present invention, is markedly reduced. Major angulation alignment errors, which are known to significantly degrade radiograph quality, are essentially eliminated with practice of the present invention.

Practice of the present invention also allows use of a wide latitude x-ray film with a 6:1 anti-scatter grid and x-ray beam energy of 90 KV or lower, while providing consistently high radiograph image quality in portable radiography. It has been found that use of the optical grid alignment system of the present invention does not interfere with the normal operation of the portable x-ray equipment, while providing focus distance and grid alignment information which can be easily assimilated. In addition, because accurate grid alignment is consistent and predictable with use of the present invention, the problem of incorrect exposure of the radiograph can be reduced. Though primarily developed for portable chest radiography, the optical alignment system of the present invention is adaptable to other types of bedside x-ray examination, including non-standard views such as lateral and decubitus projections, where accurate grid alignment is particularly important due to the large amount of scatter generated.

Although the present invention has been described with reference to selected preferred embodiments, it will be understood by those of ordinary school in this art that deletions, additions, or modifications can be made to the disclosed preferred embodiments, without departing from the spirit and scope of the present invention.

I claim:

1. A grid alignment system for use in a portable radiographic apparatus for aligning x-ray film with an x-ray source within said portable radiographic apparatus, comprising:

a grid cassette, movable relative to said x-ray source, including an x-ray film holding portion, an anti-scatter grid substantially fixed relative to said x-ray film holding portion and positionable between said x-ray film holding portion and said x-ray source, and a reflector element substantially fixed relative to said grid, said reflector element including a reflective surface for reflecting said incident light beam to produce a reflected light beam, and an imaging surface for producing images of said incident light beam and said reflected light beam, said images providing an indication of alignment between said grid cassette and said x-ray source; and a light beam projector substantially fixed relative to said x-ray source, said light-beam projector projecting said incident light beam upon said reflector element to provide said indication of alignment between said grid cassette and said x-ray source.

2. The alignment system as recited in claim 1, said reflector element being integrally formed with said grid cassette.

3. The alignment system as recited in claim 1, said reflector element being removably attached to said grid cassette.

4. The alignment system as recited in claim 1, said grid cassette further comprising an integrally formed hand hold.

5. The alignment system as recited in claim 1, said incident light beam forming an incident light line on said reflector element.

6. The alignment system as recited in claim 5, said reflective surface reflecting said incident light line to produce a reflected light line, and said imaging surface producing images of said incident light line and said reflected light line, a distance between said light line images being indicative of alignment between said grid cassette and said x-ray source.

7. The alignment system as recited in claim 5, said incident light line being substantially parallel to a longitudinal dimension of grid lines within a said anti-scatter grid.

8. The alignment system as recited in claim 1, said incident light beam forming an incident light spot on said reflector element.

9. The alignment system as recited in claim 8, said reflective surface reflecting said incident light spot to produce a reflected light spot, and said imaging surface producing images of said incident light spot and said reflected light spot, a distance between said light spot images being indicative of alignment between said grid cassette and said x-ray source.

10. The alignment system as recited in claim 1, said grid cassette further comprising:

at least one pair of radiopaque markers, a first of said at least one pair of markers being positioned on a first side of said grid, and a second of said at least one pair of markers being positioned on a second side of said grid, said at least one pair of markers being positioned to produce images of said markers on an x-ray film in said film holding portion upon exposure to x-radiation, said marker images being indicative of an amount of angulation alignment error between said x-ray source and said grid cassette.

11. The alignment system as recited in claim 1, said light beam projector comprising a semiconductor laser.

12. The alignment system as recited in claim 11, said semiconductor laser producing a light beam having a substantially elliptical cross-section, said light beam projector further comprising a cylinder lens for converting said light beam having a substantially elliptical cross-section into a fan-shaped light beam.

13. A portable x-ray apparatus which is sufficiently mobile to be brought to bedside for making radiographs of a patient, comprising:
   an x-ray source adjustable in orientation to allow the exposure of radiographs of portions of a patient in a plurality of orientations at bedside;
   a grid cassette including an anti-scatter grid and a film cassette holding portion, said grid cassette being positional relative to said x-ray source to produce radiographs of said patient;
   a light beam projector substantially fixed relative to said x-ray source, for projecting a light beam toward said grid cassette, said light beam being substantially parallel to a central x-ray beam of said x-ray source;
   a reflector element, substantially fixed relative to said grid cassette, for receiving said light beam, and for producing an indication of angulation alignment between said grid cassette and said x-ray source, said reflector element including a reflective surface for reflecting said incident light beam to produce a reflected light beam, and an imaging surface for producing images of said incident light beam and said reflected light beam, said images providing said indication of alignment between said grid cassette and said x-ray source.

14. The portable x-ray apparatus as recited in claim 13, further comprising:
   a collimator housing including a collimator light and a collimator image carrying surface which together project a shadow of said collimator image onto said patient and said grid cassette during alignment of said x-ray source and said grid cassette, said collimator image including a focus line which casts a focus indicating shadow on a surface of said grid cassette, coincidence between said light beam and said focus indicating shadow being indicative of location of said grid cassette at a proper focal distance from said x-ray source.

15. The portable x-ray apparatus as recited in claim 13, said light beam projector producing an incident light spot upon said reflector element.

16. The portable x-ray apparatus as recited in claim 15, said reflective surface reflecting said incident light spot to produce a reflected light spot, and said imaging surface producing images of said incident light spot and said reflected light spot, a distance between said light spot images being indicative of an angulation alignment error between said x-ray source and said grid cassette.

17. The portable x-ray apparatus as recited in claim 13, said light beam projector producing a substantially fan-shaped light beam which forms an incident light line upon said reflector element.

18. The portable x-ray apparatus as recited in claim 17, said reflective surface reflecting said incident light line to produce a reflected light line, and said imaging surface producing images of said incident light line and said reflected light line, a distance between said light line images being indicative of an angulation alignment error between said x-ray source and said grid cassette.

19. The portable x-ray apparatus as recited in claim 17, said incident light line being substantially parallel to grid lines within said anti-scatter grid.

* * * * *

UNITED STATES PATENT AND TRADEMARK OFFICE
CERTIFICATE OF CORRECTION

PATENT NO. : 5,241,578
DATED : August 31, 1993
INVENTOR(S) : Heber MacMahon

It is certified that error appears in the above-indentified patent and that said Letters Patent is hereby corrected as shown below:

Claim 1, column 10, line 13, change "said" to --an--.

Claim 13, column 11, line 20, change "positional" to --positionable--.

Signed and Sealed this

Twelfth Day of April, 1994

Attest:

BRUCE LEHMAN

*Attesting Officer*   *Commissioner of Patents and Trademarks*